(12) United States Patent
Hartley (10) Patent No.: US 8,344,323 B1
(45) Date of Patent: Jan. 1, 2013

(54) APPARATUS AND METHOD FOR DETECTING AND QUANTIFYING ANALYTES IN SOLUTION

(75) Inventor: Frank Thomas Hartley, Arcadia, CA (US)

(73) Assignee: Roc8Sci Co., Arcadia, CA (US)

( * ) Notice: Subject to any disclaimer, the term of this patent is extended or adjusted under 35 U.S.C. 154(b) by 0 days.

(21) Appl. No.: 13/196,340

(22) Filed: Aug. 2, 2011

Related U.S. Application Data (63) Continuation-in-part of application No. 12/157,513, filed on Jun. 11, 2008, now Pat. No. 8,022,366.

(51) Int. Cl.
*G01J 5/02* (2006.01)
*G01J 5/00* (2006.01)

(52) U.S. Cl. .................... 250/340; 250/338.1; 250/341.6

(58) Field of Classification Search .................. 250/340, 250/338.1, 339.07, 339.03, 339.04; 356/222
See application file for complete search history.

(56) References Cited

U.S. PATENT DOCUMENTS

| 5,499,095 | A * | 3/1996 | Gast et al. ..................... 356/451 |
| 6,240,306 | B1 | 5/2001 | Rohrscheib et al. |
| 7,088,441 | B2 | 8/2006 | Nahum et al. |
| 2002/0033453 | A1 | 3/2002 | Sauer et al. |
| 2004/0155668 | A1 * | 8/2004 | Hajduk et al. ................ 324/663 |
| 2008/0230698 | A1 * | 9/2008 | Simelgor et al. ........... 250/338.1 |

OTHER PUBLICATIONS

Boosalis, Fani Polyzos, "U.S. Appl. No. 12/157,513 Notice of Allowance May 18, 2011", Publisher: USPTO, Published in: US.
Boosalis, Fani Polyzos, "U.S. Appl. No. 12/157,513 Office Action Mar. 18, 2011", Publisher: USPTO, Published in: US.

* cited by examiner

*Primary Examiner* — David Porta
*Assistant Examiner* — Faye Boosalis
(74) *Attorney, Agent, or Firm* — Kaplan Breyer Schwarz & Ottesen, LLP (57) ABSTRACT

A method for identifying and quantifying one or more analytes included in a sample comprising a background solvent is disclosed. The present invention enables in-situ calibration and removal of the spectral signature of the background solvent from a composite spectrum so that the spectral features associated with the analyte(s) can be more easily and precisely identified. Further, the method enables estimation of the concentration of the analyte(s) by normalizing the spectrum based on the path length of the infrared radiation through the sample.

21 Claims, 5 Drawing Sheets

APPARATUS AND METHOD FOR DETECTING AND QUANTIFYING ANALYTES IN SOLUTION

CROSS REFERENCE TO RELATED APPLICATIONS

This case is a continuation-in-part of co-pending U.S. patent application Ser. No. 12/157,513, entitled "Non-invasive Qualitative Measurement of Chemistry of Blood and Bodily Fluids," filed Jun. 11, 2008, which is incorporated herein by reference in its entirety.

In addition, the underlying concepts, but not necessarily the language, of the following case are incorporated by reference: U.S. patent application Ser. No. 12/157,511, filed Jun. 11, 2008, entitled "Mid-IR Spectral Measurement for Real-time Identification of Analytes in an Industrial and Laboratory Setting,", which is incorporated herein by reference in its entirety.

FIELD OF THE INVENTION

The present invention relates to chemical analysis in general, and, more particularly, to analyte detection and analysis using spectrometry.

BACKGROUND OF THE INVENTION

An ability to quickly identify and quantify one or more analytes in a solution is desirable in many areas, including medical diagnostics, petroleum exploration, environmental health monitoring, and drug testing. Unfortunately, many conventional analysis systems and methods are time-intensive and can be quite complicated. In addition, many conventional analytical approaches require the use of consumable reagents or test strips, which require calibration for each use, are subject to degradation over time, often provide only a qualitative result, and can require coding.

Infrared spectroscopy represents an optical chemical analysis method that overcomes many of these drawbacks. Infrared spectroscopy interrogates a sample using an optical signal having a relatively broad wavelength range. Infrared light (electromagnetic radiation having a wavelength within the range of approximately 740 nanometers to approximately 300 microns) is typically transmitted through the sample such that each chemical constituent in the sample imparts spectral information on the outgoing optical signal. This spectral information manifests as intensity peaks at specific wavelength locations in a spectral plot of the output signal, wherein the positions, magnitudes, and inflections of these peaks (i.e., the "spectral fingerprint") are indicative of the constituent chemicals in the sample.

Initially developed for use in outer space exploration, spectral fingerprinting based on spectroscopy (infrared- and/or visible-light spectroscopy) has been used to measure Doppler shifts caused by radial velocity changes of distant suns in the search for exo-planets potentially orbiting around them. In order to effectively measure such small effects, however, a spectrometer requires careful calibration and an absolute wavelength reference. In space applications, iodine is often used for these purposes. Iodine is an attractive reference because a temperature-controlled iodine vapor cell is spectrally rich over a useful wavelength range. Specifically, iodine has sixty-seven precise and non-variant spectral features over the wavelength range from 389.5 nanometers (nm) to 681.5 nm. An iodine vapor cell is added to the optical path of the interferometer so that the light from the distant sun can pass through it. The spectral features in the light from the sun are then verniered against the iodine spectral features. The Doppler shift of the sun's spectra, therefore, can be precisely determined relative to the absolute locations of the spectral features of the iodine.

The medical industry has embraced infrared spectroscopy for some analytical applications, such as blood analysis, blood flow kinetics, brain scanning, and the like. Unfortunately, in many such applications, the use a separate calibration chemical in the analysis of a chemical mixture is highly undesirable. Often, the analytes being analyzed exist in a background solvent (typically water) at extremely low concentrations. As a result, the spectral characteristics of the background solvent swamp the spectral information of the targeted analytes making them difficult to identify and/or quantify. In addition, in many cases, the background solvent has a high absorption coefficient in the wavelength range where much of the analyte-specific spectral information is located. The addition of more spectral information by using a calibration chemical would often serve only to further confound the analysis of the sample.

Perhaps the most common medical application for which infrared spectrometry is attractive is blood analysis. Unfortunately, infrared spectroscopy of blood chemistry is complicated by the fact that water makes up approximately 80% of blood and the analytes targeted for identification have a concentration level in the parts-per-million range (or lower). Still further, water exhibits a significant absorption window over the range of wavelengths in which most analytes exhibit their strongest characteristic spectral information. As a result, identifying and quantifying an analyte, such as glucose, in blood is complicated by the fact that the spectral signature of the water in the blood masks the spectral information of the analytes.

Currently, many conventional medical analysis systems require collection of blood so that it can be held in a container of known thickness during analysis. This enables the estimation of the concentration of the analyte that is based on the known path length of the infrared light through the sample. The need to draw blood increases patient discomfort, however. It also represents a potential health risk to the caregiver. Ideally, blood analysis would be performed non-invasively by transmitting the infrared radiation through a thin-tissue region of the body, such as the ear lobe or webbing between the fingers. Unfortunately, it is extremely difficult to quantify the measured analytes in the blood in such systems due to the fact that the precise path length of the light through the tissue is indeterminate.

An ability to quantify one or more analytes in a background solution without the use of an external wavelength reference, with the potential for non-invasively measure bodily fluids, would represent a significant advance of the state-of-the-art.

SUMMARY OF THE INVENTION

The present invention enables identifying and quantifying one or more analytes included in a sample comprising a background solvent by using the background solvent itself as a wavelength reference. In accordance with the present invention, the spectral signature of the background solvent can be substantially removed from a composite spectrum based on the complete chemistry of the sample. As a result, the spectral features associated with an analyte in the sample can be more easily identified. Further, the method enables estimation of the concentration of the analyte by normalizing the spectral characteristics of the analyte to the spectral characteristics of the background solvent. In some embodiments, this normalization is enabled by the use of spectral characteristics of the background solvent, itself, to develop an absolute wavelength reference.

A method in accordance with the present invention employs pre-determined spectral information for a background solvent included in a first sample to effectively remove its contribution to the composite spectral signal that is based on all of the constituent chemicals in the first sample. Typically, the spectral information for the background solvent will dominate the composite spectral signal thereby making it difficult, if not impossible, to differentiate spectral characteristics of analytes included in the sample. Once the spectral information for the background solvent is substantially removed from the composite spectral signal, however, the spectral information based on the analytes can more easily be identified and analyzed.

In an illustrative embodiment of the present invention, a mid-infrared radiation source is driven with an electrical pulse train so that it emits pulses of mid-infrared radiation having wavelength within the range of 2.5 microns to approximately 12.5 microns. This radiation passes through a first sample, which comprises a background solvent and a first analyte, to produce a composite signal. The composite signal is then separated into discrete wavelength signals, each having a spectral width of approximately 2-3 nm.

Each wavelength signal is received by a different one of a plurality of MEMS-based detectors having a capacitance that is based on the intensity of the radiation incident upon it. Electronic circuits coupled with the detectors convert these capacitances into a composite spectral signal that represents the total chemical makeup of the first sample.

A processor receives this composite spectral signal and effectively removes the spectral contribution of the background solvent from the composite spectral signal. In order to accomplish this, the processor applies a pre-determined spectral model of the background solvent as a spectral template. The processor substantially subtracts this spectral template from the composite spectral signal to yield an output spectral signal in which the contributions from the analytes are more prominent. In other words, the "noise" in the composite spectral signal (corresponding to the background solvent) is reduced, thereby yielding an output signal having an improved signal-to-noise ratio.

In some embodiments, the pre-determined spectral model of the background solvent is developed by building a database of spectra based on: (1) pure background solvent at a plurality of temperatures over a temperature range that preferably includes the anticipated temperature at which the first sample will be analyzed; and (2) a plurality of samples containing the target analyte (or analytes), each at a different known concentration in the background solvent over a range of concentrations that preferably include the anticipated concentration of the target analyte in the first sample. In some embodiments, additional spectra are taken for pure background solvent while it is held a plurality of pressures over a pressure range that preferably includes the pressure at which the first sample will be analyzed.

In some embodiment, the spectra taken at different temperatures are used to determine temperature-related shifts in the strength of the stretch-and-bend vibrational peaks of the background solvent. In many background solvents, such as water, these shifts occur at specific wavelengths. As a result, the shifts provide an absolute wavelength reference that is used as a template for providing wavelength registration of the measured spectra.

In some embodiments, each MEMS-based detector comprises a plate having an absorbing region and an underlying electrode that is disposed on a substrate. The plate and electrode collectively define a parallel-plate capacitor whose capacitance is based on their separation. In operation, the absorbing region receives one of the wavelength signals and converts its optical energy into heat. The plate is thermally coupled with an actuator whose temperature determines the separation between the plate and the electrode. As a result, heat conveyed into the actuator from the absorbing region changes the temperature of the actuator, which, in response, changes the separation between the plate and electrode. In order to enable rapid response of the actuator, the actuator is also thermally coupled with the substrate to facilitate removal of the heat from the actuator. In some embodiments, the plate and a portion of the actuator comprise diamond, which has a high thermal conductivity.

An embodiment of the present invention comprises an apparatus comprising a spectrometer, the spectrometer comprising: (1) a source of infrared radiation, the source being dimensioned and arranged to enable illumination of a sample with the infrared radiation; (2) a wavelength separator, the wavelength separator receiving a first composite signal from the sample, the first composite signal being based on the infrared radiation and spectral characteristics of the sample, wherein the wavelength separator distributes the first composite signal into a plurality of wavelength signals; and (3) a plurality of detectors, wherein each of the plurality of detectors generates a first electrical signal based on one of the first plurality of wavelength signals, and wherein each of the plurality of detectors comprises; (i) a plate, wherein the plate comprises an absorber that converts incident light to heat; (ii) an electrode disposed on a substrate, the electrode and the plate collectively defining a parallel-plate capacitor whose capacitance is based on a first separation between the electrode and the plate; and (iii) an actuator, the actuator being dimensioned and arranged to change the first separation in response to a change in the temperature of the actuator; wherein the plate and the actuator are thermally coupled to enable transfer of heat from the plate to the actuator, and wherein the actuator and the substrate are thermally coupled to enable transfer of heat from the actuator to the substrate.

DETAILED DESCRIPTION

The present invention enables rapid, high-confidence detection and quantification of low-concentration analytes in a background solvent. Some embodiments of the present invention are particularly well suited for medical applications and environmental testing applications, wherein analysis of analytes in a water-rich environment is desired. Other embodiments of the present invention are well suited to industrial, chemical, and petrochemical applications, wherein analysis of analytes in a background solvent other than water is desired.

The present invention enables instrumentation, such as a portable/mobile instrument or 'personal' miniature nanotechnology tissue assessment device, for point-of-care diagnostic approaches that can effectively and quickly detect and quantify analytes in a water-rich environment. Embodiments of the present invention can facilitate blood analysis for the detection of the levels of cholesterol, glucose, glycated hemoglobin and ketone bodies, which would have great diagnostic importance in the treatment of coronary heart diseases, diabetes mellitus, and other such diseases. Additional embodiments of the present invention can facilitate the treatment of diabetes-related health issues through rapid and accurate quantification of glucose and/or other blood components—in some cases, non-invasively through a thin-tissue region of a patient. Such embodiments would enable better diagnosis and treatment of diseases, as well as potentially improving the quality-of-life for the patients themselves by reducing the stress and pain associated with disease monitoring.

In addition to blood-based analysis, the present invention also enables embodiments suitable for dental environments, which involve samples with even higher water content and lower concentration of water-born analytes. The present invention therefore, enables measurement of chemicals that could indicate host pathology and/or potentially bacterial/viral antigenic molecules, which enables measurement of disease activity, including squamous-cell carcinoma markers, to screen for head, neck and throat cancers, etc., evaluation of root canal sterility, testing for periodontal disease stability/progression, differentiation between lichen planus and systemic lupus, oral carcinoma detection—even early lesions, etc.

The present invention also enables detection of health conditions of a patient that could be hazardous to the healthcare profession providing treatment. For example, embodiments of the present invention enable detection of major viruses and bacteria/fungi that can act as secondary pathogens in HIV. A dentist could be made aware, therefore, of bacterial and viral species contained in the patient's mouth, including HIV, HSV1, HSV2, EBV, CMV, *Prevotella intermedia, Porphyromonas gingivalis, Streptococcus mutans*, etc., thus enabling protective measures to be taken.

Some embodiments of the present invention enable detection of a wider range of drugs than is now possible due to their spectral 'finger-prints' in the MIR spectral region. As a result, detection and quantification of drugs required for Road-Side Drug Testing is enabled, such as alcohol, cocaine, amphetamines, cannabinoids, opiates, methadone, phencyclidine (PCP), benzodiazepines, as well as new synthetic "designer drugs" as they emerge.

This capability is particularly attractive for detecting "doping" in the sports world. World Anti-Doping Agency (WADA), for example, has outlined six classes of prohibited substances: stimulants; narcotics; anabolic agents/steroids; diuretics; peptide hormones and related compounds; and other restricted drugs. These classes include more than four hundred substances and thousands of related compounds. Embodiments of present invention can be customized to detect any individual drug throughout this wide array. Further, embodiments of the present invention are suited to applications in other areas as well, such as the criminal justice area, employment screening, and the road safety arena.

Still further, some embodiments of the present invention enable detection of water-born contaminants in environmental applications, such as watershed protection, soil sampling, environmental protection, hazardous material detection and cleanup, and the like.

Figure 1:
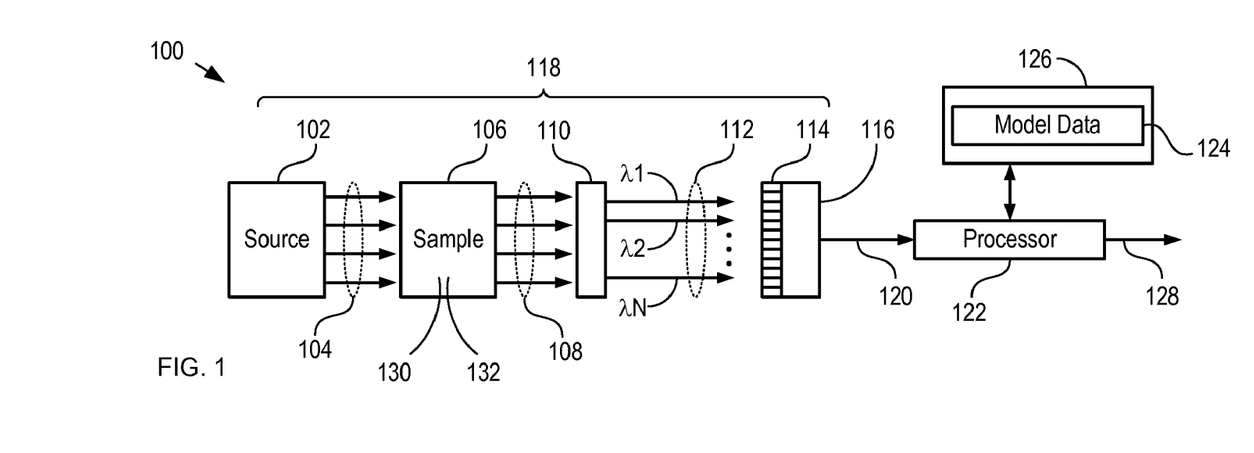
FIG. 1 depicts a schematic diagram of a chemical analysis system in accordance with an illustrative embodiment of the present invention.

An organic solvent embodiment of the present invention would be Gasoline which contains up to 80% of $C_5$ to $C_{12}$ paraffin hydrocarbons (with between 4 and 12 carbon atoms per molecule), the dominant solvents, up to 30% of aromatic compounds, up to 13% of olefins, more recently up to 10% ethanol, and minor quantities of many substances, such as antiknock agents, antioxidants, metal deactivators, antirust additives, anti-icing agents, pre-ignition additives, upper cylinder lubricants, dyes, and water. FIG. 1 depicts a schematic diagram of a chemical analysis system in accordance with an illustrative embodiment of the present invention. System 100 comprises source 102, wavelength separator 110, detector array 114, detector circuitry 116, and processor 120. Source 102, wavelength separator 110, detector array 114, and detector circuitry 116 collectively define spectrometer 118. System 100 employs infrared radiation to optically interrogate sample material and generate spectral information that is characteristic of one or more analytes in the sample. For exemplary purposes, system 100 is described herein as a chemical analysis system for detecting and quantifying glucose in a blood sample.

Figure 2:
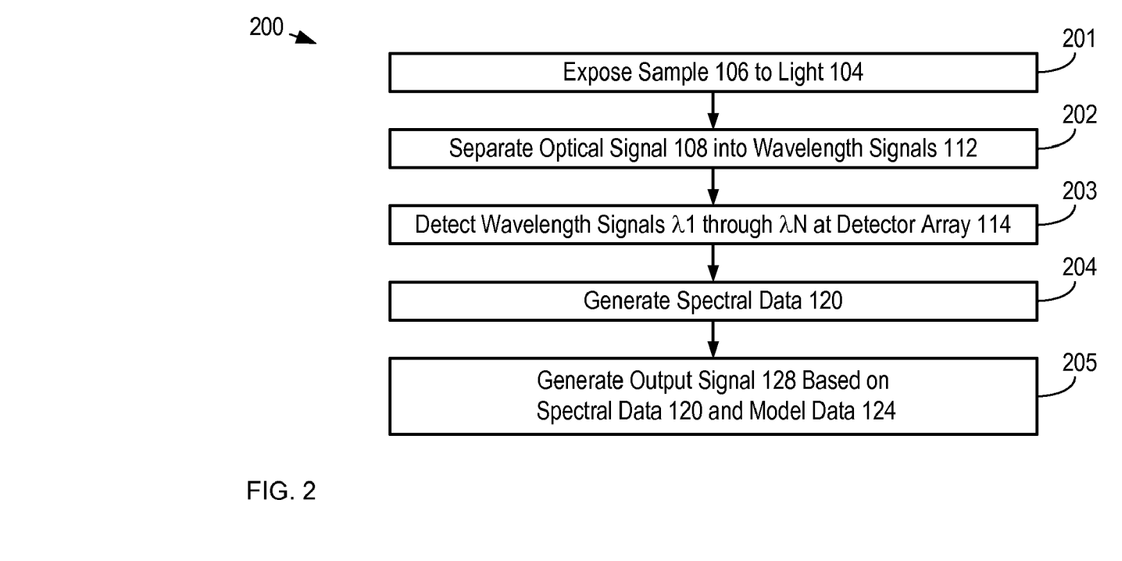
FIG. 2 depicts operations of a method suitable for detecting and quantifying an analyte in accordance with the illustrative embodiment of the present invention.

FIG. 2 depicts operations of a method suitable for detecting and quantifying an analyte in accordance with the illustrative embodiment of the present invention. Method 200 begins with operation 201, wherein sample 106 is exposed to light 104. Light 104 is mid-infrared radiation emitted by source 102. Method 200 is described herein with continuing reference to FIG. 1 as well as reference to FIGS. 2-8.

Source 102 is a source for providing radiation in the mid-infrared wavelength range.

Figure 3:
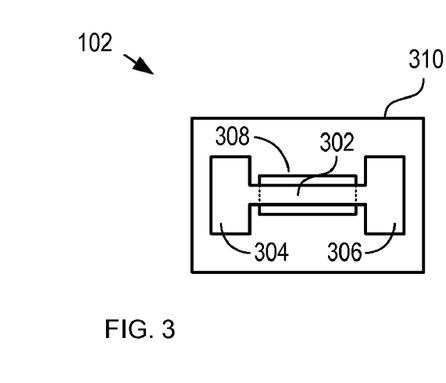
FIG. 3 depicts a schematic drawing of a top view of an infrared source in accordance with the illustrative embodiment of the present invention.

FIG. 3 depicts a schematic drawing of a top view of an infrared source in accordance with the illustrative embodiment of the present invention. Source 102 comprises filament 302 and terminals 304 and 306. Although the illustrative embodiment comprises a source of mid-infrared radiation, it will be clear to one skilled in the art, after reading this Specification, how to specify, make, and use alternative embodiments of the present invention that comprise a source of radiation having a wavelength within any of the near-, mid-, and far-infrared ranges.

Filament 302 is a beam of silicon carbide having a thickness of approximately 2 microns, a width of approximately 5 microns, and a length of approximately 30 microns.

Filament 302 is suspended above cavity 308, which is formed in substrate 310. Filament 302, cavity 308, and terminals 304 and 306 are formed on substrate 310 using conventional surface micromachining techniques. In response to a flow of electrical current between terminals 304 and 306 (i.e., through filament 302), filament 302 becomes hot and emits mid-infrared radiation.

The materials of source 102 and the dimensions of filament 302 described herein in are merely exemplary and it will be clear to one skilled in the art, after reading this Specification, that source 102 and filament 302 can have a wide range of dimensions and/or comprise any of a wide range of suitable materials including, without limitation, metals, semiconductors, silicon, single-crystal silicon, graphite, dielectrics, and the like.

Although the present invention is suitable for operation at any infrared wavelength, the use of mid-infrared radiation (MIR) affords some embodiments of the present invention with particular advantages the detection and quantification of one or more analytes contained in the sample material. For the purposes of this Specification, including the appended claims, "mid-infrared radiation" (MIR) is defined as electromagnetic radiation having a wavelength within the range of approximately 2.5 microns to approximately 12.5 microns.

In the prior art, MIR is not typically used for chemical analysis in spectrometry-based systems because many host materials (e.g., solvent fluids, blood, saline, bodily tissue, etc.) have a well-known absorption window in the mid-infrared wavelength range. Because of this absorption window, MIR does not significantly penetrate sample material in many applications, such as blood serum analysis, glucose monitoring, and the like.

Prior-art systems, therefore, are typically based on near-infrared light (i.e., wavelengths within the range of approximately 800 nm to approximately 2500 nm), where light does penetrate sample material to a usable depth. Unfortunately, the resultant spectral information from target chemicals and compounds in the sample material is typically overwhelmed by the background spectral information associated with the host material. In fact, the identification and quantitative analysis of target analytes and chemicals is precluded by the fact that their signature information is simply "lost in the noise" of spectral information of the host material.

It is an aspect of some embodiments of the present invention, in contrast to the conventional philosophy of the prior art, that in some embodiments MIR can be surprisingly well suited for sample interrogation. In fact, the use of MIR affords some embodiments of the present invention with substantial advantage over prior-art systems because the mid-infrared wavelength region contains a great deal of information about the structure of chemical compounds that is heretofore underutilized. In order to exploit this "fingerprint" region of the electromagnetic spectrum, however, the spectral information of the host material must be effectively removed from the composite spectrum of an optically interrogated sample. The present invention achieves this by subtracting a "known" spectrum of the host material, at the temperature and pressure of the sample, from the composite signal. Once the spectral information of the host material is effectively removed, the remaining spectral information can be readily analyzed to yield chemical identification and quantization.

One skilled in the art will recognize that an uncooled infrared detector is well suited for detecting a change in the intensity of incident infrared radiation; however, it is typically poorly suited to sensing the absolute intensity level of received infrared radiation. As a result, it has been typical in the prior art to modulate the infrared radiation that is received by such a detector by means of an external modulator, such as a mechanical beam-chopper (e.g., a rotating blade, mechanical shutter, etc.). Mechanical beam-choppers, however, are relatively large, costly, and represent a reliability issue.

Further, prior-art systems typically employ a conventional incandescent light or specialty lamp to emit infrared light. Unfortunately, such conventional infrared sources emit light over too wide a wavelength range. As a result, light outside the measurement wavelength range generates spectral noise by parasitic heating of components of the system. This spectral noise degrades the sensitivity and accuracy of prior-art systems. In some prior-art systems spectral filters are included to narrow the emission bandwidth of their infrared sources.

By virtue of the small size of its emissive filament, however, source 102 can exhibit all of the desired characteristics of an externally modulated, spectrally narrow, infrared source without the added cost and complexity associated with external modulation and added wavelength filters. Since filament 302 has very low thermal mass, its temperature closely tracks the magnitude of electrical current that flows through it. Direct modulation of filament 302, therefore, can be used to induce it to emit a modulated optical signal directly. In some embodiments, electrical pulse shaping and current regulation are also used to further enable filament 302 to provide a high radiant output having a high temperature-slew rate, little or no thermal hysteresis, and extremely low power consumption.

In order to avoid time delays associated with the heating and cooling of a cover window, in some embodiments, an optical window or other protective cover plate does not cover filament 302. In some applications, however, it is necessary to protect the filament and a suitable, substantially transparent cover window is positioned over filament 302.

Although the illustrative embodiment comprises a source that emits infrared radiation having a range of wavelengths, it will be clear to one skilled in the art, after reading this specification, how to specify, make, and use alternative embodiments of the present invention wherein source 102 emits other than infrared radiation having a range of wavelengths. For example, in some embodiments of the present invention, source 102 is a tunable source that tunes narrow-wavelength emitted radiation across the range of wavelengths. In some embodiments, source 102 comprises an array of sources, each of which emits radiation having a different wavelength.

Returning to FIG. 1, sample 106 is a suitable volume of blood that is contained in a container suitable for enabling optical interrogation by light 104, such as containers described in detail in U.S. patent application Ser. No. 12/157,511. Sample 106 comprises background solvent 130 and target analyte 132. One skilled in the art will recognize that in the case of blood, background solvent 130 is typically water. As described above, for exemplary purposes only, analyte 132 is selected as glucose.

It should be noted that blood is merely an example of a sample material for which the present invention is applicable and, therefore, is useful for describing the illustrative embodiment. The present invention is suitable for identification and/or quantification of analytes contained in a wide range of liquid solvents, such as water, saline, oils, alcohols, acids, and the like. Sample materials for which the present invention is applicable include, without limitation, petroleum products, saliva, bodily fluids, bodily tissue, biological matter, sera, pharmaceutical products, water, and the like.

Some embodiments of the present invention enable interrogation of biological matter in-vivo—for example, by passing light 104 through an ear lobe, webs between fingers/toes, pinch of loose flesh, or other relatively thin portion of living tissue. In such embodiments, therefore, sample 106 does not require an external container. As discussed below and with respect to FIGS. 7 and 8, variations in the path length of light 104 through 106 from sample to sample do not significantly impact chemical analysis of sample 106 because the present invention normalizes measured spectral information to remove the effect of this path length on the measurements.

After it transits sample 106, light 104 is imprinted with the spectral information of sample 106 and is received by wavelength separator 110 as composite spectrum 108. Composite spectrum 108 comprises spectral information for both background solvent 130 and analyte 132 (as well as any other analytes contained in sample 106).

It should be noted that the illustrative embodiment, source 102 and sample 106 are arranged such that light 104 is transmitted through sample 106 to produce a transmission spectrum; however, it will be clear to one skilled in the art, after reading this specification, how to specify, make, and use alternative embodiments of the present invention wherein light 104 is reflected from sample 106 to produce a reflection spectrum. In some embodiments, sample 106 is contained in a fixture (cuvette, pipette, or similar suitable fixture) such that light 104 transits sample 106, is reflected, and transits sample 106 a second time on its path toward wavelength separator 110.

At operation 202, wavelength separator 110 spatially separates the wavelength components of composite spectrum 108.

Figure 4:
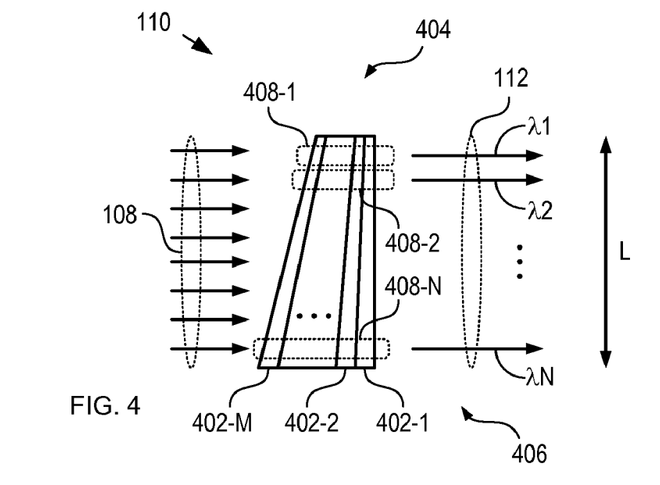
FIG. 4 depicts a schematic drawing of a cross-sectional view of a wavelength separator in accordance with the illustrative embodiment of the present invention.

FIG. 4 depicts a schematic drawing of a cross-sectional view of a wavelength separator in accordance with the illustrative embodiment of the present invention. Wavelength separator 110 is a spatial wavelength filter that receives composite spectrum 108 and provides wavelength signal 112. Wavelength signal 112 comprises wavelength signals λ1 through λN, which are arranged in a linear array along length, L, of wavelength separator 110. In order to effectively detect and quantify many analytes, system 100 must be able to differentiate spectral signals with a granularity of approximately 2 wave numbers over the 10 micron-wide spectral range from 2.5 to 12.5 microns. Wavelength separator, therefore, separates composite spectrum 108 into thousands of individual wavelength signals.

Wavelength separator 110 comprises layers 402-1, through 402-M (referred to, collectively, as layers 402), which are alternating layers of silicon dioxide and silicon nitride. The thickness of each of layers 402 increases linearly along length, L, from end 404 to end 406. The thickness of each of layers 402 at end 404 is equal to one-quarter of wavelength λ1 (within the material of each layer). In similar fashion, the thickness of each of layers 402 at end 406 is equal to one-quarter of wavelength λN. As a result, layers 402 collectively define a linear array of wavelength filters 408-1 through 408-N (referred to, collectively, as wavelength filters 408) that are equally spaced along length, L. Each of wavelength filters 408 passes only one of wavelength signals λ1 through λN and blocks transmission of the remainder of composite spectrum 108. For example, wavelength filter 408-1 passes only wavelength λ1, wavelength filter 408-2 passes only wavelength λ2, etc. As a result, wavelength separator 110 provides a linear array of wavelength signals where each wavelength signal uniquely includes one spectral slice of composite spectrum 108.

Although in the illustrative embodiment, layers 402 are alternating layers of silicon dioxide and silicon nitride, one skilled in the art will recognize that the materials used for layers 402 can be selected from a myriad of alternative materials.

In order to obtain suitable wavelength granularity, the finesse of each of wavelength filters 108 is within the range of approximately 2 nm to approximately 3 nm. As a result, in some embodiments, wavelength separator 110 comprises many layers 402. In some cases, in fact, the number of layers, M, exceeds 1000.

Although the illustrative embodiment comprises a wavelength separator that is a multi-layer wedge filter, it will be clear to one skilled in the art, after reading this specification, how to specify, make, and use alternative embodiments of the present invention wherein wavelength separator 110 is other than a multi-layer wedge-filter. Wavelength separators suitable for use with the present invention include, without limitation: wavelength dispersive elements, such as prisms, diffraction gratings, holographic elements; wavelength filter elements, such as discrete wavelength filter arrays, tunable filter arrays; and combinations thereof, such as tunable diffractive gratings, rotatable diffraction gratings, rotatable prisms, and the like.

At operation 203, wavelength signals λ1 through λN are received by detector array 114.

Figure 5:
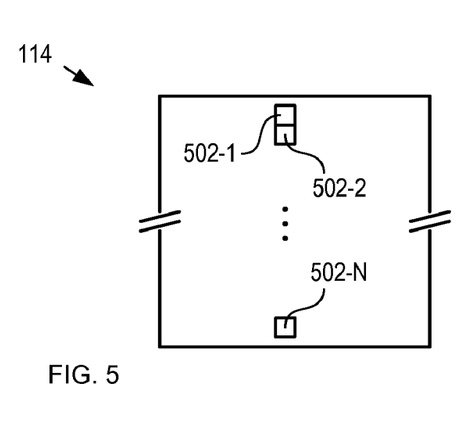
FIG. 5 depicts a schematic drawing of a top view of a detector array in accordance with the illustrative embodiment of the present invention.

FIG. 5 depicts a schematic drawing of a top view of a detector array in accordance with the illustrative embodiment of the present invention. Detector array 114 comprises detectors 502-1 through 502-N (referred to, collectively, as detectors 502). Each detector 502 comprises a capacitor whose capacitance is based on the intensity of light incident upon it. In some embodiments, each detector 502 is substantially thermally and mechanically isolated from its neighboring detectors to mitigate thermal and mechanical crosstalk.

Detectors 502 are arranged such that each detector receives a different one of wavelength signals λ1 through λN.

Figure 6A:
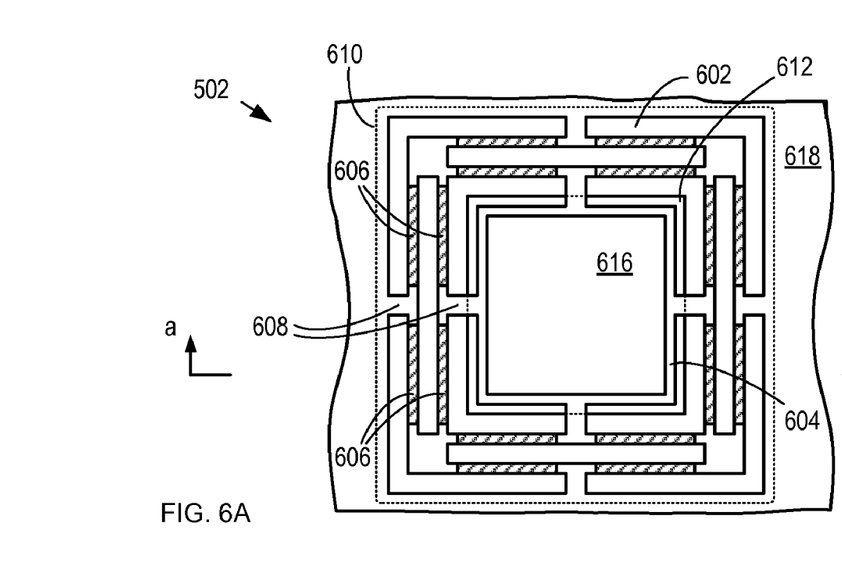
FIGS. 6A and 6B depict schematic drawings of top and side views, respectively, of a detector in accordance with the illustrative embodiment of the present invention.
Figure 6B:
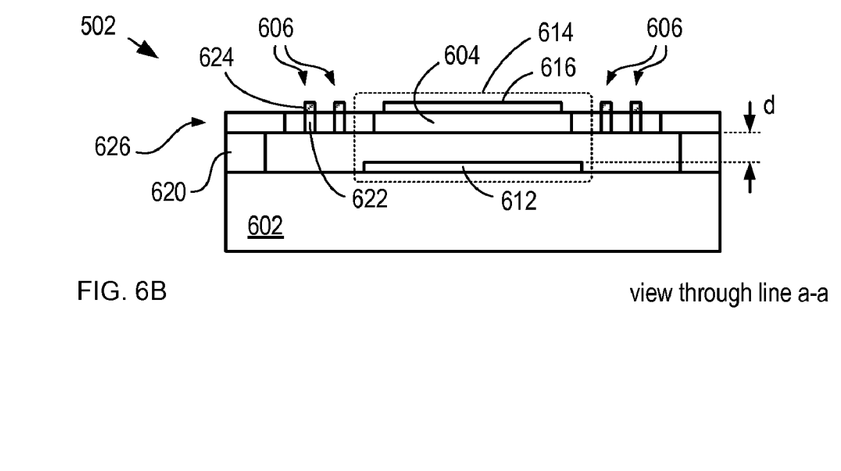

FIGS. 6A and 6B depict schematic drawings of top and side views, respectively, of a detector in accordance with the illustrative embodiment of the present invention. Detector 502 is a capacitive sensor whose capacitance depends on the separation between a center region of a membrane and an electrode located on an underlying substrate. This separation is, in turn, based on the intensity of radiation that is incident on the detector. Detector 502 comprises substrate 602, plate 604, elements 606, and tethers 608.

Substrate 602 is a conventional silicon substrate. In some embodiments, substrate 602 is comprises another material, such as a semiconductor, ceramic, metal, plastic, composite material, glass, and the like. Substrate 602 comprises electrode 612. Electrode 612 is a region of electrically conductive material, such as a metal, that is disposed on substrate 602 directly under plate 604. As a result, plate 604 and electrode 612 collectively define parallel-plate capacitor 614. In some embodiments, electrode 612 is electrically connected to ground potential. In some embodiments, substrate 606 is a metal plate and electrode 612 is a portion of an electrically conductive substrate.

Plate 604, elements 606, and tethers 608 are formed from membrane 610 via conventional Micro-Electro-Mechanical Systems (MEMS) fabrication techniques. Membrane 610 is a portion of layer 626, which is disposed on spacer layer 620, which is further disposed on substrate 602. Layer 626 is a layer of diamond having a thickness of approximately 1 micron. In some embodiments, layer 626 comprises another suitable material that has a relatively high thermal conductivity. In some embodiments, layer 626 has a thickness other than 1 micron. One skilled in the art will recognize that many materials are suitable for use in layer 626.

Plate 604 is a substantially square plate that is held above electrode 612 via elements 606 and tethers 608. Plate 604 and electrode 612 are separated by gap, d, which, in the absence of light, is equal to the thickness of spacer layer 620. Plate 602 has a size suitable for receiving an entire wavelength signal from wavelength separator 110 without receiving a significant amount of a second wavelength signal. In some embodiments, plate 604 has a shape other than square. Plate 604 comprises absorber 616. Absorber 616 comprises a material having high absorptivity to enable absorption of mid-IR radiation (e.g., tungsten, etc.). In some embodiments, absorber 616 is a region of plate 604 that has been treated to increase its absorptivity. In some embodiments, plate 604 comprises a material having a relatively high absorptivity and, therefore, absorber 616 is merely a portion of plate 604.

Elements 606 collectively define an actuator that controls the separation, d, between plate 604 and electrode 612. Each of elements 606 comprises a bi-material layer structure comprising tether 622 and material 624, which is disposed on tether 622. Material 624 has a thermal expansion coefficient that differs from that of the material of membrane 610 (and, therefore, tether 622).

Each of tethers 608 is a portion of membrane 610. Tethers 608 collectively mechanically couple plate 608 to elements 606 and mechanically couple elements 606 to field region 618. Field region 618 is disposed on spacer layer 620, which mechanically and thermally couples field region 618 to substrate 602.

In response to a change of temperature of elements 606, a difference in the amount of thermal expansion of the first and second materials induces the elements to change their curvature. As a result, elements 606 either bend upward from substrate 602 or downward toward substrate 602 (depending on the relative thermal expansion coefficients of the two materials and the direction of temperature change). Since each of elements 606 has one end that is fixed at field region 618, this bending changes the height of the opposite end of each of the elements above substrate 602.

In operation, detector 502 receives one of wavelength signals λ1 through λ N. Plate 604 converts the energy of the received wavelength signal into thermal energy, heating plate 604. Heat from plate 604 is conducted to elements 606 via tethers 608, increasing the temperature of elements 606. Their increased temperature causes elements 606 to change the separation between plate 604 and electrode 606, changing the capacitance of capacitor 614.

In addition to supporting plate 604 above electrode 612, elements 606 and tethers 608 also thermally couple plate 604 to substrate 602 through field region 618. The materials and dimensions of detector 502 are selected to enable it to response quickly to a change in the intensity of radiation incident upon it. In the illustrative embodiment, for example, detector 502 is designed with a time constant of 15 milliseconds. A fast time constant arises from the fact that membrane 610 is very thin and therefore has a very low thermal capacity. Further, since membrane 610 comprises material having high thermal conductivity, and plate 604, elements, 606, and tethers 608 are thermally coupled; heat readily flows into and out of elements 606 quickly. This provides elements 606 with a rapid physical response to a change in the intensity of incident radiation.

Although in the illustrative embodiment, plate 604, elements 606, and tethers 608 are formed from a substantially continuous membrane, it will be clear to one skilled in the art, after reading this specification, how to specify, make, and use alternative embodiments of the present invention wherein are plate 604, elements 606, and tethers 608 are formed using different surface micromachining techniques. In some embodiments, for example, at least one of plate 604, elements 606, and tethers 608 comprises material that is different than the material of at least one other of these components.

At operation 204, the capacitance of each of detectors 502 is converted by detector circuitry 116 into an electrical signal based on the intensity of the wavelength signal received by that detector. These electrical signals collectively define composite spectral data 120. Detector circuitry 116 comprises a plurality of conventional circuits for converting a capacitance into an electrical signal, such as a circuit typically included in a conventional read-out integrated circuit (ROIC).

At operation 205, processor 122 generates output signal 128 based on composite spectral data 120 and model data 124. In some embodiments, output signal 128 is further based on the pressure of sample 106. Output signal 128 includes identification of analyte 132 and, in some embodiments, an estimation of the concentration of analyte 132 in sample 106.

Processor 122 is a conventional computer processor capable of executing instructions, running programs, and accessing database 126, which is stored in a conventional memory module. In some embodiments, processor 122 comprises the memory module that contains database 126.

Figure 7:
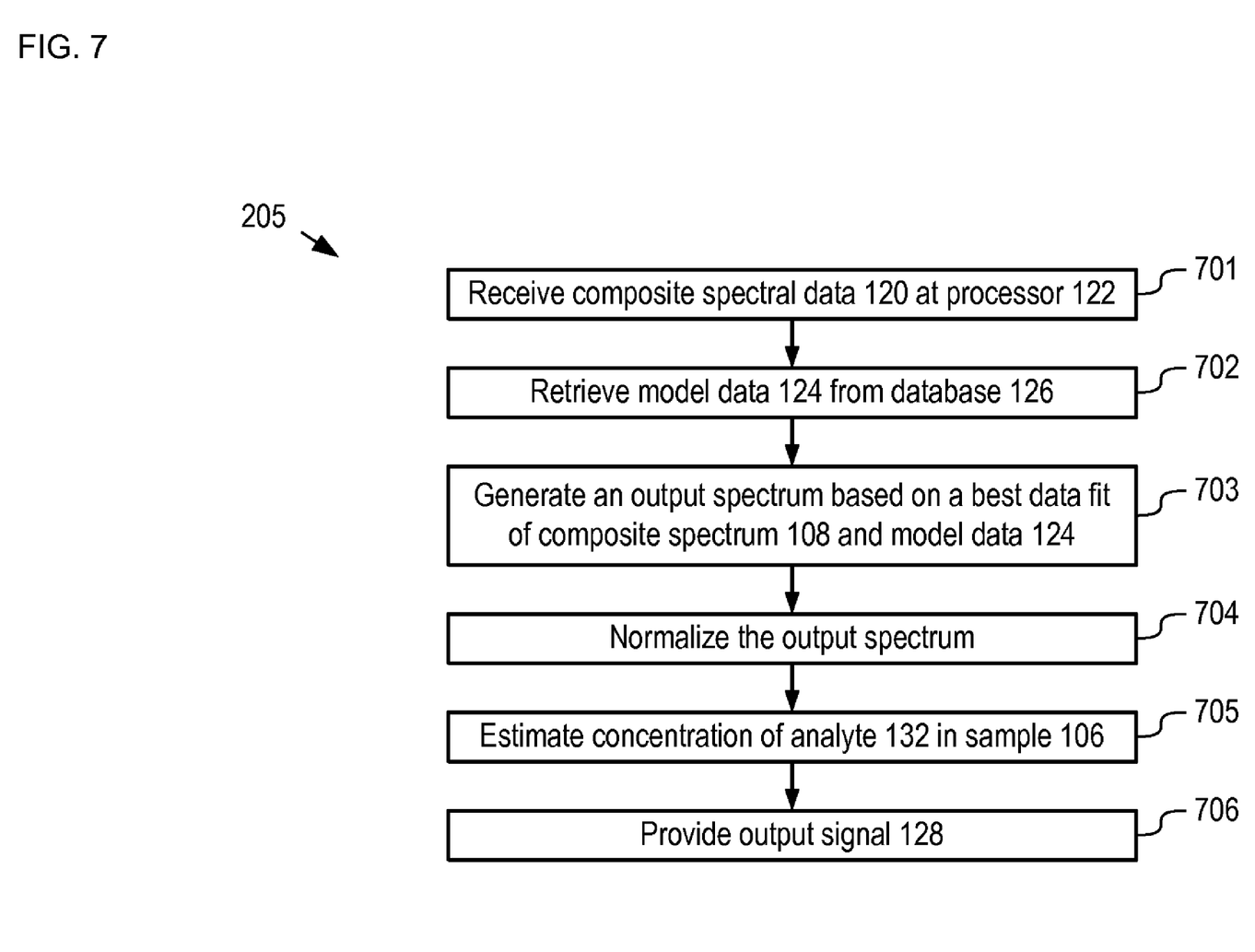
FIG. 7 depicts sub-operations suitable for use in operation 205.

FIG. 7 depicts sub-operations suitable for use in operation 205. Operation 205 begins with sub-operation 701, wherein processor 122 receives composite spectral data 120 from detector circuitry 116.

At sub-operation 702, processor 122 accesses database 126 to obtain pre-determined model data 124. Model data 124 comprises spectral information for background solvent 130 and analyte 132. The spectral information for background solvent 130 includes spectra measured for samples of pure background solvent at different temperatures over a temperature range. Preferably, this temperature range includes the temperature at which sample 106 is analyzed. In some embodiments, the spectral information for background solvent 130 also includes spectra measured for samples of pure background solvent at different pressures over a pressure range. Preferably, this pressure range includes the pressure at which sample 106 is analyzed. The spectral information for analyte 132 includes spectra measured on samples of substantially pure analyte diluted in background solvent at different concentrations over a concentration range. Preferably, this concentration range includes the anticipated concentration of analyte 132 in sample 106.

For example, in the illustrative embodiment, sample 106 is blood; therefore, background solvent 130 is water. One skilled in the art will recognize that, in addition to dominating composite spectral data 120, water also has the highest absorbance over the MIR wavelength range. This serves to further obscure the spectral information for target analyte 132 (as well as any other chemical constituents in sample 106) within composite spectral data 120. Model data 124, therefore, is provided as comprising spectra for water at a plurality of temperatures over an expected measurement temperature range (e.g., the range of temperatures from approximately 10° C. to approximately 80° C.) and an expected measurement pressure range (e.g., the range of pressures from approximately 0.5 atmospheres to approximately 1.5 atmospheres).

Model data 124 provides processor 122 with an in-situ frequency reference and precise spectral template that represents a disproportionately large contributor to composite spectral data 120.

Model data 124 also includes spectral information for glucose (i.e., target analyte 132). In some embodiments, model data 124 also includes spectral information for other analytes anticipated to be in sample 106. One skilled in the art will recognize that each removal of spectral information for another constituent chemical in sample 106 from composite spectral data 120 typically improves the quality of analysis for target analyte 132.

In some embodiments, model data 124 is pre-stored in database 126 prior to analysis of sample 106 via method 200. In some embodiments, however, model data 124 is developed and stored in database 126 as part of a calibration procedure performed as part of method 200.

Figure 8:
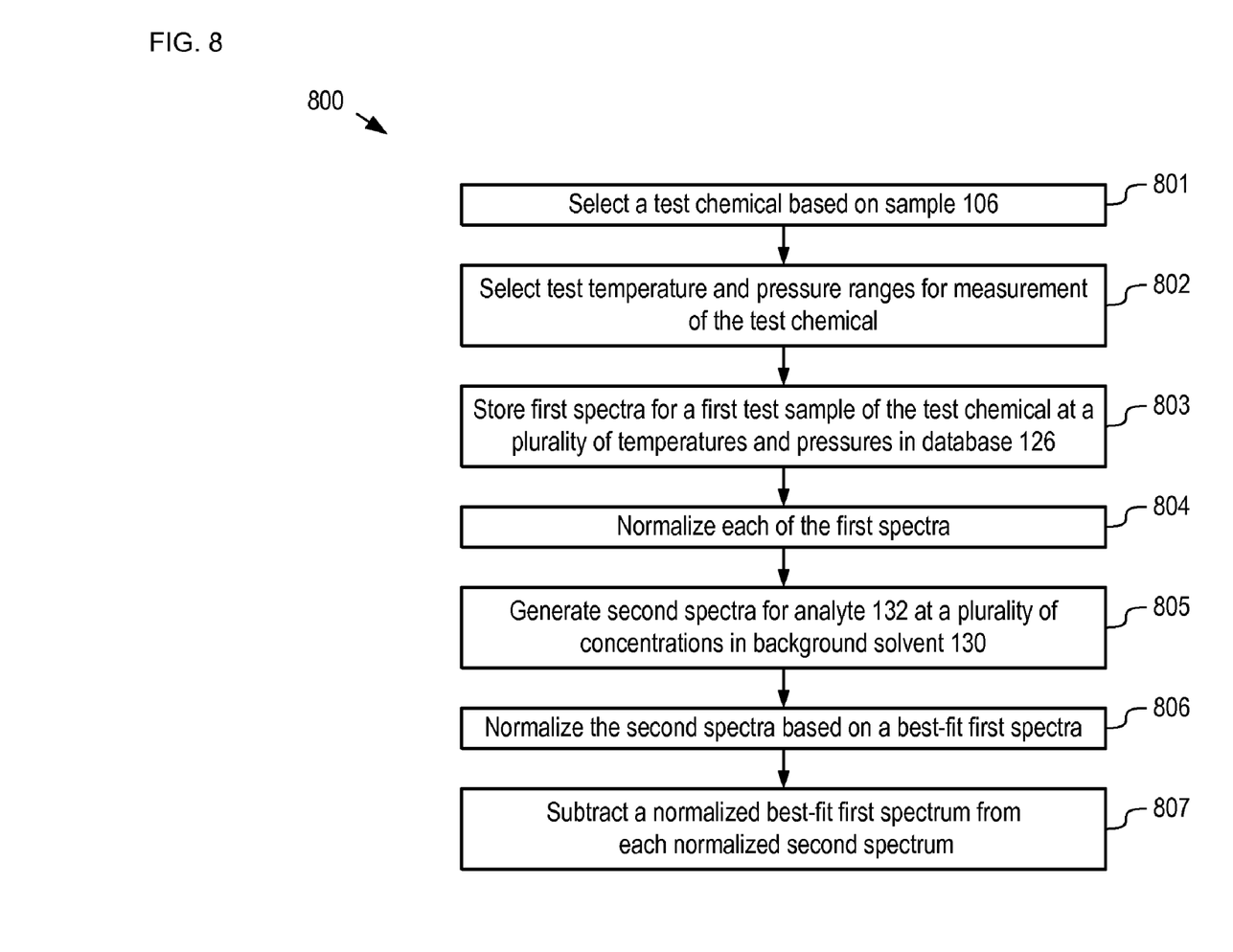
FIG. 8 depicts operations of a calibration procedure suitable for developing model data in accordance with the present invention.

FIG. 8 depicts operations of a calibration procedure suitable for developing model data in accordance with the present invention. Method 800 begins with operation 801, wherein a test chemical based on background solvent 130 is selected. In the illustrative embodiment, this test chemical is selected as de-ionized water.

It is an aspect of the present invention that an in-situ frequency reference and precise spectral template can be developed based on a plurality of spectra measured for the background solvent at a variety of temperatures. The frequency reference and template can then be used to effectively remove of the spectral information for the background solvent from a composite spectrum that spectral information for one or more analytes in the background solvent.

The present invention exploits the fact that many background solvents, such as water, have spectral characteristics that include stretch-and-bend vibrational peaks. In liquid water, for example, an increase in the temperature of the water induces the molecular stretch vibrations to shift to higher frequencies. This occurs due to a weakening of the hydrogen bonds and strengthening of the covalent O—H bonds, which causes them to vibrate at higher frequencies. A decrease in the temperature of the water, however, induces the intramolecular vibrations to shift to lower frequencies, while the molecular bend vibration peak shifts to lower frequencies and becomes both narrower and stronger. For many background solvents, such as water, these stretch-and-bend vibrational peaks are located at wavelengths that are precise and non-variant. As a result, the temperature-induced changes in the spectra provide an absolute wavelength reference for the spectra, which enables development of a precise spectral template that can be applied to all spectra measured for samples that include that background solvent.

It should be noted that the most common hydrogen isotope accounts for more than 99.98% of hydrogen in water (HDO exists only in low concentrations of ~0.03%, $D_2O$ in even lower concentrations of ~0.000003%, and tritium $T_2O$ only in minute quantities). Further, the most common oxygen isotope $^{16}O$ accounts for 99.76% ($^{17}O$ exists only in low concentrations of ~0.04%, and $^{18}O$ exists in concentrations of ~0.2% of water molecules). As a result, one skilled in the art will recognize, after reading this specification, that water isotopologues do not significantly impact the ability to use water as an in-situ absolute wavelength reference.

At operation 802, a test temperature range and a test pressure range are selected. The test temperature range is selected to include an expected temperature of sample 106 during its analysis by system 100. The test pressure range is selected to include an expected pressure of sample 106 during its analysis by system 100.

At operation 803, a plurality of first spectra are measured for a first test sample consisting of the test chemical, wherein each of the plurality of first spectra corresponds to each of a plurality of temperatures within the test temperature range and each of a plurality of pressures within the test pressure range. The spectra are then stored in database 126.

At operation 804, each of the plurality of first spectra is normalized to mitigate their dependency on the path length of light 104 through sample 106. The normalized first spectra are then stored in database 126.

At operation 805, each of a plurality of second spectra is measured for analyte 132, wherein each spectrum of the plurality of second spectra is measured using a solution having a different concentration of analyte 132 in background solvent 132. These solutions contain substantially only analyte 132 and background solvent 130.

At operation 806, for each of the plurality of second spectra, one of the plurality of first spectra is determined as a best-fit first spectrum for that second spectrum. Each second spectrum is then normalized with respect to its corresponding best-fit first spectrum.

At operation 807, the spectral information of the corresponding normalized best-fit first spectrum is subtracted from each normalized second spectrum. This results in a set of spectra for the pure suspended analyte alone, wherein the magnitude of each spectrum is a measure of the concentration of analyte in its corresponding sample. The resultant analyte-specific spectra are stored in database 126.

The spectra generated in operations 803 through 807 collectively represent model 124. In some embodiments, operations 804 through 807 include measuring spectra for one or more additional analytes expected to be in sample 106. The spectra for the additional analytes are measured and normalized in the same manner as those for analyte 132 and further enrich the database of spectra in model 124. One skilled in the art will recognize, after reading this specification that, by enriching model 124, the precision of the analysis of sample 106 can be improved.

Returning now to FIG. 7, at sub-operation 703, processor 122 performs a multidimensional best data fit based on composite spectrum 108 and model data 124. The data fit produces an output spectrum comprising peaks for background solvent 130 and analyte 132. The data fit also improves the signal-to-noise ratio in the output spectrum.

At operation 704, the output spectrum is normalized based on the best-fit water spectrum. As a result, the magnitudes of the spectral peaks associated with analyte 132 enable an estimation of the concentration level of analyte 132 in sample 106 that is substantially independent of the path length of light 104 through sample 106.

At sub-operation 705, processor 122 estimates the concentration of analyte 132 in sample 106 based on the magnitudes of the spectral peaks for analyte 132 in the normalized output spectrum. Such spectroscopic analysis for a range of concentrations for analyte 132 enables development of a complete chemometric model and calibration for the analyte.

At operation 706, processor 122 provides a chemometric model for analyte 132 as output signal 128.

The description herein is based on the use of spectrometer 118, which is a system for interrogating a sample using mid-infrared radiation via a MEMS-based source and detector. It should be noted, however, that the present invention is suitable for use with any spectrometer that is capable of generating a composite spectral data 120. As a result, although the illustrative embodiment of the present invention comprises spectrometer 118, it will be clear to one skilled in the art, after reading this specification, how to specify, make, and use alternative embodiments of the present invention wherein composite spectral data 120 is provided to processor 122 by a spectrometer other than spectrometer 118.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. An apparatus comprising a spectrometer, the spectrometer comprising:
   (1) a source of mid-infrared radiation that is within the wavelength range of approximately 2.5 microns to approximately 12.5 microns, the source being dimensioned and arranged to enable illumination of a sample with the infrared radiation;
   (2) a wavelength separator, the wavelength separator receiving a first composite signal from the sample, the first composite signal being based on the infrared radiation and spectral characteristics of the sample, wherein the wavelength separator distributes the first composite signal into a plurality of wavelength signals; and (3) a plurality of detectors, wherein each of the plurality of detectors generates a first electrical signal based on one of the first plurality of wavelength signals, and wherein each of the plurality of detectors comprises;

(i) a plate, wherein the plate comprises an absorber that converts incident light to heat;

(ii) an electrode disposed on a substrate, the electrode and the plate collectively defining a parallel-plate capacitor whose capacitance is based on a first separation between the electrode and the plate; and (iii) an actuator, the actuator being dimensioned and arranged to change the first separation in response to a change in the temperature of the actuator;

wherein the plate and the actuator are thermally coupled to enable transfer of heat from the plate to the actuator, and wherein the actuator and the substrate are thermally coupled to enable transfer of heat from the actuator to the substrate.

2. The apparatus of claim 1, each actuator comprising a first bi-material element having a first end and a second end, the first end being mechanically coupled with the plate and the second end being substantially immovable with respect to the substrate, wherein a change in the temperature of the first bi-material element induces motion of the first end with respect to the substrate.

3. The apparatus of claim 2 wherein the first material comprises diamond.

4. The apparatus of claim 2, each actuator comprising a second bi-material element having a third end and a fourth end, the third end being mechanically coupled with the plate and the fourth end being substantially immovable with respect to the substrate, wherein a change in the temperature of the second bi-material element induces motion of the third end with respect to the substrate, and wherein the plate, first bi-material element, and second bi-material element are dimensioned and arranged such that motion of the first end and third end induces the plate to move with respect to the electrode while remaining substantially parallel with the electrode.

5. The apparatus of claim 1 wherein the substrate is electrically conductive.

6. The apparatus of claim 1 wherein the source is dimensioned and arranged to emit the infrared radiation as a pulse of infrared radiation.

7. The apparatus of claim 6 wherein the source emits the infrared radiation in response to a drive signal that is an electrical pulse.

8. The apparatus of claim 1 further comprising:

(4) a processor; and (5) a database comprising a plurality of spectra for each of a first chemical constituent and a second chemical constituent, wherein the sample comprises the first chemical constituent and the second chemical constituent;

wherein the processor is dimensioned and arranged to receive the plurality of wavelength signals and provide an output signal that is based on the plurality of wavelength signals and the plurality of spectra.

9. A method comprising:

providing a first composite spectral signal that is based on a first sample comprising a first chemical constituent and a second chemical constituent, wherein the first composite spectral signal includes a first spectral signal and a second spectral signal, the first spectral signal being based on the first chemical constituent and the second spectral signal being based on the second chemical constituent;

providing a first spectral model that is based on spectra corresponding to the first chemical constituent and spectra corresponding to the second chemical constituent;

processing the first composite spectral signal and the first spectral model to reduce the magnitude of the first spectral signal; and estimating a first concentration of the second chemical constituent in the first sample.

10. The method of claim 9 further comprising providing wavelength registration for the first composite signal based a wavelength reference, wherein the wavelength reference is based on temperature-related changes in a plurality of spectral peaks in the spectra corresponding to the first chemical constituent.

11. The method of claim 9 wherein the first composite spectral signal is provided by operations comprising:

providing a first composite light signal by exposing the first sample to infrared radiation that comprises a first range of wavelengths, wherein the first composite light signal comprises spectral information that is based on the first sample;

distributing the first composite light signal into a plurality of wavelength signals, wherein the plurality of wavelength signals collectively span the first range of wavelengths; and receiving each of the plurality of wavelength signals at a different one of a plurality of detectors, wherein the plurality of detectors collectively generates the first composite spectral signal.

12. The method of claim 11 wherein each of the plurality of detectors generates a portion of the first composite spectral signal by operations comprising:

receiving one of the plurality of wavelength signals at a plate comprising an absorber, wherein the absorber converts received wavelength signal into heat, and wherein the heat is based on the intensity of the wavelength signal;

controlling a separation between the plate and an electrode, wherein the plate and the electrode collectively define a capacitor whose capacitance is based on the separation, and wherein the separation is based on the temperature of an actuator that is thermally coupled with the plate; and enabling the flow of heat from the actuator;

wherein the portion of the first composite spectral signal is based on the capacitance of the capacitor.

13. The method of claim 9 further comprising normalizing the first composite spectral signal, wherein the first composite spectral signal is normalized based on the spectra corresponding to each of the first chemical constituent, and wherein the first concentration for the second chemical constituent is estimated based on the magnitude of the normalized first composite spectral signal.

14. The method of claim 13 wherein the first sample further comprises a third chemical constituent, and wherein the first composite spectral signal further includes a third spectral signal that is based on the third chemical constituent, and wherein the first spectral model is based further on spectra corresponding to the third chemical constituent, and further wherein the method further comprises estimating a second concentration for the third chemical constituent in the first sample based on the magnitude of the normalized first composite signal.

15. The method of claim 9 further comprising providing the first spectral model, wherein the first spectral model is provided by operations comprising:
- generating a plurality of first spectra, wherein each of the plurality of first spectra is based substantially only the first chemical constituent and wherein each of the plurality of first spectra is based on the first chemical constituent at a different temperature;
- storing the plurality of first spectra in a database;
- generating a plurality of second spectra, wherein each of the plurality of second spectra is generated by measuring a different one of a plurality of third samples that consist essentially of the first chemical constituent and the second chemical constituent, and wherein each of the plurality of third samples has a different concentration of the second chemical constituent;
- determining a best-fit first spectrum for each of the plurality of second spectra;
- normalizing each of the plurality of second spectra based on its corresponding best-fit first spectrum;
- modifying each of the plurality of second spectra by substantially removing its corresponding best-fit first spectrum; and
- storing the plurality of modified second spectra in the database.

16. The method of claim 15 further comprising establishing a wavelength reference based on a temperature dependence of at least one wavelength peak that is included in each of the plurality of first spectra.

17. The method of claim 16 wherein the temperature dependence of the at least one wavelength peak is based on stretch-and-bend vibrations in the first chemical constituent.

18. A method comprising:
- providing a first composite light signal by exposing a first sample to mid-infrared radiation that comprises a first range of wavelengths, wherein the first sample comprises a first chemical constituent and a second chemical constituent, and wherein the first composite light signal comprises spectral information that is based each of the first chemical constituent and the second chemical constituent;
- distributing the first composite light signal into a plurality of wavelength signals, wherein the plurality of wavelength signals collectively span the first range of wavelengths; and
- providing a first composite spectral signal that comprises a plurality of first output signals, wherein each of the plurality of output signals is provided by operations comprising:
- receiving each of the plurality of wavelength signals at a different one of a plurality of detectors, wherein each of the detectors provides a first output signal that is based on the intensity of its received wavelength signal, and wherein each of the detectors provides the first output signal by operations comprising;
- converting incident light into heat;
- conveying at least a portion of the heat to an actuator, wherein the actuator controls the capacitance of a capacitor based on the temperature of the actuator, wherein the actuator is thermally coupled with a substrate such that the flow of heat from the actuator to the substrate is facilitated; and
- providing the first output signal based on the capacitance of the capacitor.

19. The method of claim 18 further comprising providing the infrared radiation, wherein the infrared radiation is provided by operations comprising:
- providing a first electrical signal to a source, wherein the source is dimensioned and arranged to convert electrical energy into infrared radiation characterized by the first range of wavelengths; and
- modulating the first electrical signal such that the first electrical signal comprises a plurality of pulses of electrical energy.

20. The method of claim 18 further comprising generating a second output signal that is based on first composite spectral signal and a first spectral model, wherein the first spectral model is based on a plurality of first spectra that are based on substantially only the first chemical constituent and a plurality of second spectra that are based on the second chemical constituent.

21. The method of claim 20 further comprising providing the first spectral model by operations comprising:
- generating the plurality of first spectra, wherein each of the plurality of first spectra is based substantially only the first chemical constituent and wherein each of the plurality of first spectra is based on the first chemical constituent at a different temperature;
- storing the plurality of first spectra in a database;
- generating the plurality of second spectra, wherein each of the plurality of second spectra is generated by measuring a different one of a plurality of third samples that consist essentially of the first chemical constituent and the second chemical constituent, and wherein each of the plurality of third samples has a different concentration of the second chemical constituent;
- determining a best-fit first spectrum for each of the plurality of second spectra;
- normalizing each of the plurality of second spectra based on its corresponding best-fit first spectrum;
- modifying each of the plurality of second spectra by substantially removing its corresponding best-fit first spectrum; and
- storing the plurality of modified second spectra in the database.

* * * * *